(12) United States Patent
Matei et al.

(10) Patent No.: US 8,684,009 B2
(45) Date of Patent: Apr. 1, 2014

(54) SYSTEM FOR DETERMINING RELATIVE DISTANCE(S) AND/OR ANGLE(S) BETWEEN AT LEAST TWO POINTS

(75) Inventors: Eusebiu Matei, Valencia, CA (US); Lawrence J. Karr, Santa Monica, CA (US); Joseph H. Schulman, Santa Clarita, CA (US)

(73) Assignee: Alfred E. Mann Foundation for Scientific Research, Santa Clarita, CA (US)

( * ) Notice: Subject to any disclaimer, the term of this patent is extended or adjusted under 35 U.S.C. 154(b) by 3059 days.

(21) Appl. No.: 10/920,554

(22) Filed: Aug. 18, 2004

(65) Prior Publication Data

US 2005/0104577 A1 May 19, 2005

Related U.S. Application Data

(60) Continuation-in-part of application No. 10/391,424, filed on Mar. 17, 2003, now abandoned, which is a division of application No. 09/677,384, filed on Sep. 30, 2000, now Pat. No. 6,564,807, which is a division of application No. 09/048,827, filed on Mar. 25, 1998, now Pat. No. 6,164,284, which is a continuation-in-part of application No. 09/030,106, filed on Feb. 25, 1998, now Pat. No. 6,185,452.

(60) Provisional application No. 60/497,419, filed on Aug. 22, 2003, provisional application No. 60/039,164, filed on Feb. 26, 1997, provisional application No. 60/042,447, filed on Mar. 27, 1997.

(51) Int. Cl.
*A61B 19/00* (2006.01)

(52) U.S. Cl.
USPC .......................................................... 128/899

(58) Field of Classification Search
USPC ................................... 600/300; 128/897–899
See application file for complete search history.

(56) References Cited

U.S. PATENT DOCUMENTS

| 4,945,305 A | 7/1990 | Blood |
| 4,986,280 A | 1/1991 | Marcus et al. |
| 5,193,539 A | 3/1993 | Schulman et al. |
| 5,193,540 A | 3/1993 | Schulman et al. |
| 5,312,439 A | 5/1994 | Loeb |

(Continued)

FOREIGN PATENT DOCUMENTS

DE 3932405 4/1991

OTHER PUBLICATIONS

WO 94/04938, Great Britain, Bladen.*

(Continued)

*Primary Examiner* — Christine Matthews
(74) *Attorney, Agent, or Firm* — Malcolm J. Romano

(57) ABSTRACT

Systems and method utilizing microelectronic devices for determining relative positions such as distances and/or angles between at least two points is described. The points may be locations of parts of the body such as the fingers on a person's hand. A first microelectronic device is adapted to emit magnetic signals and at least a second microelectronic device is adapted to receive the magnetic signals, wherein a controller is adapted to communicate with the first and second microelectronic devices. The second microelectronic device and/or the controller are adapted to determine a distance and angle between the first and the second microelectronic devices based on the strength of the magnetic signals received by the second microelectronic device.

12 Claims, 3 Drawing Sheets

(56) References Cited

U.S. PATENT DOCUMENTS

| | | | |
|---|---|---|---|
| 5,711,299 A * | 1/1998 | Manwaring et al. | 600/417 |
| 5,831,260 A | 11/1998 | Hansen | |
| 5,953,683 A | 9/1999 | Hansen et al. | |
| 6,164,284 A | 12/2000 | Schulman et al. | |
| 6,185,452 B1 | 2/2001 | Schulman et al. | |
| 6,208,894 B1 | 3/2001 | Schulman et al. | |
| 6,261,247 B1 | 7/2001 | Ishikawa et al. | |
| 6,315,721 B2 | 11/2001 | Schulman et al. | |
| 6,400,139 B1 | 6/2002 | Khalfin | |
| 6,528,991 B2 | 3/2003 | Ashe | |
| 6,564,807 B1 | 5/2003 | Schulman et al. | |
| 6,592,518 B2 * | 7/2003 | Denker et al. | 600/300 |
| 6,624,626 B2 | 9/2003 | Khalfin | |
| 6,690,963 B2 | 2/2004 | Ben-Haim | |
| 2002/0161415 A1 * | 10/2002 | Cohen et al. | 607/48 |
| 2002/0198472 A1 | 12/2002 | Kramer | |
| 2002/0198604 A1 | 12/2002 | Schulman et al. | |

OTHER PUBLICATIONS

Aravamudhan, Getting to Know Wireless Networks and Technology, Jul. 4, 2003, pp. 1-4, Publisher: Informit.com, Published in: Internet.

Telecommunication Systems, 2002, pp. 492-493, Publisher: Encyclopedia Britannica, Published in: USA.

Troyk, et al, Development of Bion Technology for Funcational Electrical Stimulation: Bidirectional Telemetry, 2001 Proceeding of the 23rd Annual EMBS International Conference, Oct. 25, 2001, pp. 1317-1320, Publisher: IEEE, Published in: Istanbul, Turkey.

Loeb, et al, Bion Implants for Therapeutic and Funcational Electrical Stimulation, Neural Prostheses for Restoration of Sensor and Motor Function, 2000, pp. 1-26, Publisher: CRC Press, Published in: Boca Raton, FL.

Loeb, et al, Bion System for Distributed Neural Prosthetic Interfaces, 2001, pp. 1-23, Published in: Los Angeles, CA.

* cited by examiner

US 8,684,009 B2

SYSTEM FOR DETERMINING RELATIVE DISTANCE(S) AND/OR ANGLE(S) BETWEEN AT LEAST TWO POINTS

This application claims the benefit of U.S. Provisional Application No. 60/497,419 filed on Aug. 22, 2003. This application is a continuation-in-part of U.S. patent application Ser. No. 10/391,424, filed Mar. 17, 2003; now abandoned which is a divisional of U.S. patent application Ser. No. 09/677,384, filed Sep. 30, 2000, now U.S. Pat. No. 6,564,807; which is a divisional of U.S. patent application Ser. No. 09/048,827, filed Mar. 25, 1998, now U.S. Pat. No. 6,164,284; which is a continuation-in-part of U.S. patent application Ser. No. 09/030,106, filed Feb. 25, 1998, now U.S. Pat. No. 6,185,452; which claims the benefit of U.S. Provisional Application No. 60/039,164, filed Feb. 26, 1997. Additionally, U.S. patent application Ser. No. 09/048,827, filed Mar. 25, 1998, now U.S. Pat. No. 6,164,284, claims the benefit of U.S. Provisional Application No. 60/042,447, filed Mar. 27, 1997. The subject matter of all of the aforementioned applications and patents are hereby incorporated by reference herein in their entirety.

BRIEF DESCRIPTION OF THE DRAWINGS

Corresponding numerals indicate corresponding elements throughout the several views of the drawings.

DETAILED DESCRIPTION OF THE PREFERRED EMBODIMENTS

In accordance with exemplary embodiments, systems and method utilizing microelectronic devices (MEDs) for determining relative positions such as distances and/or angles between at least two points is described. For example, the points may be locations of parts of the body such as the fingers on a person's hand. By determining the relative positions of the fingers, it is possible to determine whether the person is making a fist, an open hand or any other form in between. Moreover, the relative positions may be the distance(s) of certain objects from each other. By measuring the magnetic field strength between at least two microelectronic devices the distance(s) and/or the angle(s) between various points in the body or inanimate objects may be calculated.

Each microelectronic device can be a microstimulator and/or a microsensor. For example, a class of injectable/implantable microelectronic devices described in U.S. Pat. Nos. 5,193,539, 5,193,540, 5,312,439, 6,164,284, 6,185,452, 6,208,894, 6,315,721, 6,564,807 and incorporated by reference herein provide for stimulation of biological tissue or sensing of signals from biological tissue such as nerves or muscles as well as physiologic parameters such as body temperature. Each device includes electrical stimulation circuitry and electrodes configured in a form that is suitable for injection by means of a hypodermic needle or insertion tool. The devices can be leadless or have leads attached to them. Furthermore, each device may communicate through wireless or wired communication networks. In the case of wireless networks, microelectronic devices receive power by either inductive coupling to an externally applied electromagnetic field or by means of an internal rechargeable battery. They receive digital command signals by telemetry. The packaging and materials of the microelectronic device are selected and designed to protect its electronic circuitry from the body fluids and to avoid damage to the electrodes and the surrounding tissues from the presence and operation of the microelectronic device in those tissues. In this regard the microelectronic devices are hermetically sealed and unaffected by body fluids.

Figure 1:
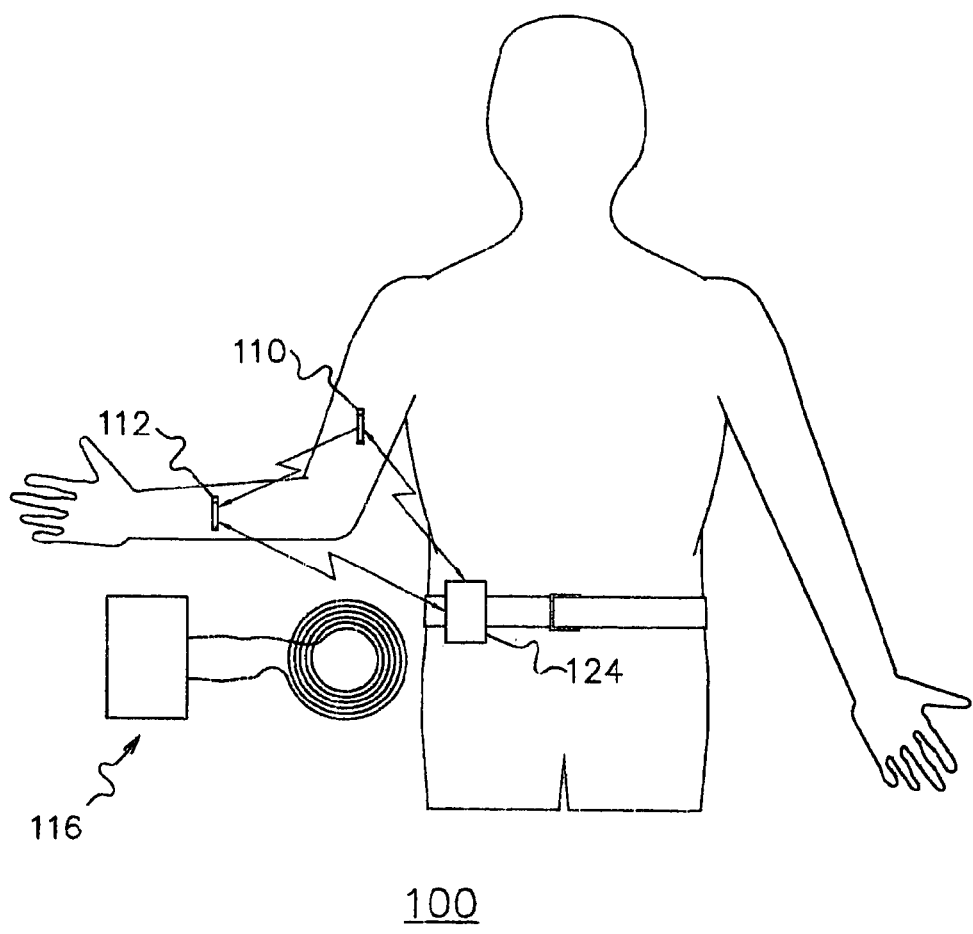
FIG. 1 is an illustration of a first system in accordance with the first exemplary embodiment of the present invention.

FIG. 1 is an illustration of a first system 100 in accordance with a first exemplary embodiment of the invention showing a first microelectronic device 110 and a second microelectronic device 112 communicating with a controller 124. In the present embodiment, the first microelectronic device 110 is adapted to emit magnetic signals and the second microelectronic device 112 is adapted to receive the magnetic signals from the first microelectronic device 110. The first and the second microelectronic devices may have similar or even identical structure and circuitry. This allows for more flexibility and scalability of the system. The controller 124, while communicating with the first and the second microelectronic devices, can assign either the first or the second microelectronic device to transmit/emit magnetic signals or receive the same. In this manner, for example, the first microelectronic device 110 can operate as a transmitter/emitter and the second microelectronic device 112 can operate as a receiver.

Referring to FIG. 1, in the first exemplary embodiment, the first system may, for example, be arranged such that the first microelectronic device 110 is implanted in the biceps area of a person and the second microelectronic device 112 is implanted in the forearm area of the person with the controller 124 attached to the belt or the waist area of the person for convenience. The controller 124, in the alternative, may be implanted in the body of the person. An external electronic device 126 is also shown which is adapted to transmit power to the first and the second microelectronic devices and also transmit command signals to the controller 124. The microelectronic devices may be either RF-powered or may include a rechargeable battery or a long-lasting primary cell. Examples of the RF-powered and the battery-powered microelectronic devices contemplated in the embodiments of the present invention are described in U.S. Pat. Nos. described above and incorporated by reference herein.

In the embodiments of the present invention, it is contemplated that magnetic signals instead of radio frequency (RF) signals are emitted from the first microelectronic device 110 and received by the second microelectronic device 112. It is known that magnetic signals are attenuated over distance in accordance to the cube law. At distances away from a source of magnetic field, the strength of the magnetic field is reduced according to the following formula: $H = H_o \times (1/d)^3$ wherein H is the strength of the magnetic field at a distance (d) away from the source of the magnetic field H and $H_o$ is a magnetic field strength at a reference distance. In contrast, the RF field attenuates as a linear function in accordance to the following formula: $H = H_o \times (1/d)$; $E = E_o \times (1/d)$ where E is the electric field component of the RF field and $E_o$ is an electric field strength at a reference distance. The embodiments of the present invention advantageously utilize the emission and reception of magnetic field signals between the microelectronic devices. Magnetic signals are less prone to interferences from external sources. It should be noted that generally there are more RF signal interference sources in the environment than there are magnetic field interference sources. Moreover, since the magnetic field signals are reduced in strength over distance at a much higher rate than the RF signals, then there are less chances that external magnetic field sources in the vicinity of the second microelectronic device will interfere with the reception of emitted magnetic signals from the first microelectronic device. The use of the magnetic signals has the further advantage that it propagates better in body tissue than the RF signals.

According to the first embodiment, after implanting the first and the second microelectronic devices in the body by utilizing either a hypodermic needle or an insertion tool, a fitting or calibration routine is performed. The calibration routine involves generating magnetic signals by the first device and measuring the strength of the magnetic signals at the second device and also physically measuring the corresponding distances between the two devices at various points. A correlation table is provided based on the corresponding magnetic signal strengths and the distances between the two devices. The values of the correlation table may be stored in any set of receiving microelectronic devices, such as the second microelectronic device 112 or the controller 124.

As described above, the first microelectronic device 110 emits magnetic signals to be received by the second microelectronic device 112. Upon receiving the magnetic signals from the first device, the second device 112 measures the strength of the magnetic signal and based on the correlation table can calculate the distance between the two devices and correspondingly the distance between the two parts of the body, such as the biceps and the forearm. As a result of the distance measurement, the position and the angle of the forearm relative to the biceps is determined, for example, whether the arm is fully extended or bent. It is further contemplated that the strength of the magnetic signal measured by the second device may be communicated to the controller 124 where it can similarly perform the distance and angle computations instead of the second device 112.

Figure 2:
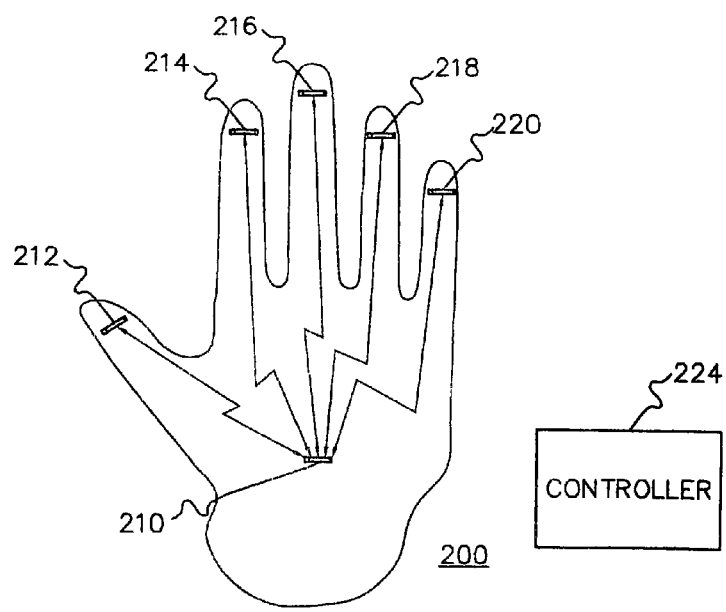
FIG. 2 is an illustration of a second system in accordance with the second exemplary embodiment of the present invention.

FIG. 2 is an illustration of a second system 200 in accordance with the second exemplary embodiment of the invention. The second system 200 comprises a first microelectronic device 210 a plurality of second microelectronic devices 212-220 and a controller 224 in communication with the first microelectronic device and the plurality of the second microelectronic devices. In the second exemplary embodiment, the first microelectronic device 210 is adapted to emit a magnetic signal having a first frequency and the plurality of second microelectronic devices 212-220 are adapted to receive the magnetic signal having the first frequency. The first microelectronic device 210 and the plurality of the second microelectronic devices 212-220 may have similar or even identical structure and circuitry as described above in connection with the first exemplary embodiment. Similar to the first exemplary embodiment, the controller 224, while communicating with the first and the plurality of second microelectronic devices, can assign either the first or any of the plurality of second microelectronic devices to transmit/emit magnetic signals or receive the magnetic signals. This allows for the ability to reconfigure the system for any desired arrangement.

Referring to FIG. 2, in the second exemplary embodiment, the second system may, for example, be an arrangement wherein the first microelectronic device 210 is implanted in the palm of a hand and the plurality of second microelectronic devices 212-220 are implanted in the fingers. The controller 224 may be positioned in any desired location such as on a belt of the person. It should be noted that the arrangement suggested in the second exemplary embodiment may be implanted in any other location in the body where a distance between and/or angle measurements of the body parts is desired.

With respect to the second exemplary embodiment, the first microelectronic device 210 emits magnetic signals having a first frequency and the plurality of second microelectronic devices 212-220 receive the magnetic signals. The plurality of second microelectronic devices 212-220 measure the strength of the received magnetic signals. The values of the strength measurements of the magnetic signals are compared to the values in the correlation table obtained by a method of calibration described earlier. By comparing the aforementioned values, the distance and/or angle measurement between the first microelectronic device 210 and the plurality of second microelectronic devices 212-220 are determined. By determining the distance and/or angle of the positions of fingers on a hand, the movements and the various forms that a hand can take is determined.

Figure 3:
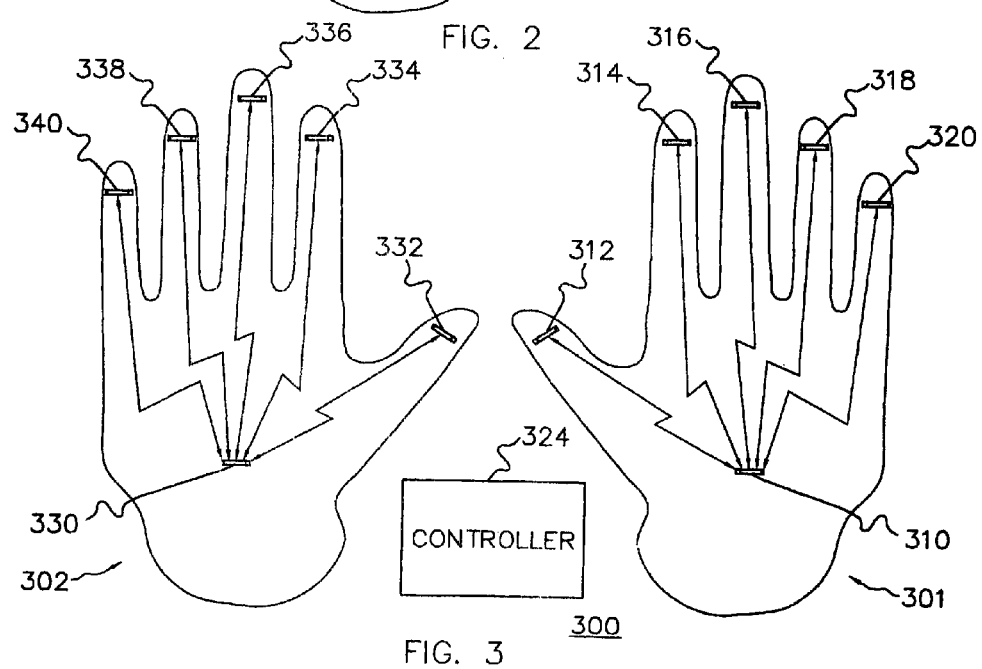
FIG. 3 is an illustration of a third system in accordance with the third exemplary embodiment of the present invention.

FIG. 3 is an illustration of a third system 300 in accordance with a third exemplary embodiment of the invention. The third system 300 broadly comprises a first subsystem and a second subsystem and a controller 324 in communication with the first and the second subsystem. The first subsystem 301 comprises a first microelectronic device 310 adapted to emit magnetic signals having the first frequency and a plurality of second microelectronic devices 312-320 adapted to receive the magnetic signals having the first frequency. The second subsystem 302 comprises a third microelectronic device 330 adapted to emit magnetic signals having a second frequency and a plurality of fourth microelectronic devices 332-340 adapted to receive the magnetic signal having a second frequency. The controller 324 communicates with the first microelectronic device, the plurality of second microelectronic devices, the third microelectronic device and the plurality of fourth microelectronic devices and through communicating with these devices it configures them such that any device may operate as source of emitting magnetic signals with a specific frequency or any device may receive the magnetic signals. It should be noted that in all of the exemplary embodiments described the distance measurement operation can be performed by either the receiving microelectronic device or the controller.

In the third system of the third exemplary embodiment, each receiving microelectronic device such as microelectronic devices 312-320 or microelectronic devices 332-340 comprises a resonator circuit in a form of an LC tank. The resonators are tuned to a central frequency Fo with a predetermined narrow bandwidth allowing for the first and the second frequencies to fall within the respective resonator bandwidth and be received and detected by each receiving microelectronic device. The microelectronic devices 312-320 and microelectronic devices 332-340 each have a digital signal processor (DSP) circuitry and each selectively processes the received magnetic signals such that the microelectronic devices 312-320 detect the magnetic signals having the first frequency and the microelectronic devices 332-340 detect the magnetic signals having the second frequency. In this manner, the two subsystems do not interfere with each other when brought close together. It should be noted that when there are multiple subsystems, namely, more than two, the present embodiment provides for multiple frequency channels wherein each subsystem communicates on a specific frequency, thereby avoiding potential interferences.

It should also be noted that in all of the exemplary embodiments described, a communication scheme such as a time-division-multiple-access (TDMA) may be implemented. For example, in order to achieve a robust communication between each receiving microelectronic device and the controller, the controller commands each microelectronic device to communicate with the controller at different predetermined time periods. This is performed where the controller transmits a global time base signal to all receiving microelectronic devices, wherein the global signal synchronizes the timing of transmission of signals from the receiving microelectronic devices in discrete time slots in a single frequency channel. In the alternative, a frequency-division-multiple-access (FDMA) or a code-division-multiple-access (CDMA) communication format between the controller and the receiving microelectronic devices may be implemented. In this case, the controller communicates with each of the receiving microelectronic devices on a different frequency.

Figure 4:
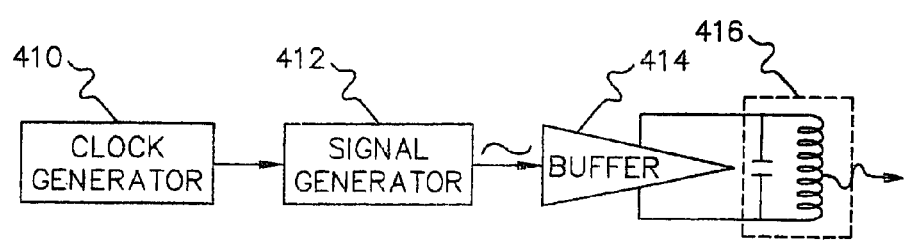
FIG. 4 is an illustration of an exemplary schematic block diagram of an emitter/transmitter portion of a microelectronic device.

FIG. 4 is an illustration of an exemplary schematic block diagram of an emitter/transmitter portion of a microelectronic device. Broadly, the emitter/transmitter portion of the microelectronic device comprises a clock generator 410, signal generator 412, a buffer 414, and an LC tank 416.

Figure 5:
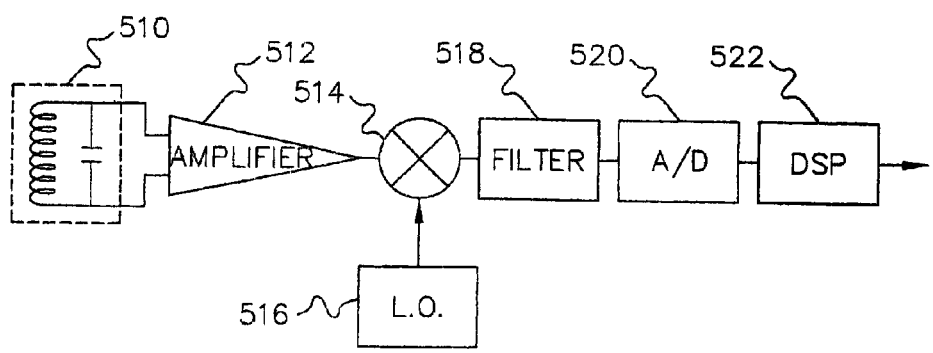
FIG. 5 is an illustration of an exemplary schematic block diagram of a receiver portion of a microelectronic device in accordance with the present invention.

FIG. 5 is an illustration of an exemplary schematic block diagram of a receiver portion of a microelectronic device. Broadly, it comprises an LC tank 510, an amplifier 512, a mixer 514 with an associated local oscillator 516, a filter 518, an analog-to-digital (AID) 520 converter and DSP 522.

It should be noted that any of the embodiments of the microelectronic devices and the controller described herein may be implanted subcutaneously or percutaneously in a body of a living organism or placed on the surface of the body. Generally, when the apparatus is implanted subcutaneously, it utilizes wireless communication although in some circumstances it may utilize wired communication with the external unit. The dimensions of the microelectronic device are less than about 100 mm and 10 mm longitudinally (axial) and laterally respectively. This provides for a more efficient injection of the device into the body.

While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

What is claimed is:

1. A system for determining relative positions of body parts, the system comprising:
    a first implantable microelectronic device adapted to emit magnetic signals having a first frequency;
    a plurality of second implantable microelectronic devices adapted to receive the magnetic signals having the first frequency;
    a controller in communication with the first implantable microelectronic device and the plurality of the second implantable microelectronic devices.

2. A system of claim 1, wherein the controller commands each of the plurality of second implantable microelectronic devices to communicate with the controller at different predetermined time periods.

3. A system of claim 1, wherein the controller commands each of the plurality of second implantable microelectronic devices to communicate with the controller on different frequencies according to a frequency-division-multiple-access (FDMA) communication format.

4. The system of claim 1, wherein each of the plurality of second implantable microelectronic devices measures the strength of the received magnetic signals and wherein each one of the plurality of second implantable microelectronic devices is capable of determining the distance between itself and the first implantable microelectronic device.

5. The system of claim 4, wherein each of the plurality of second implantable microelectronic devices transmits the measurement of the strength of the received magnetic signals to the controller and wherein the controller determines each distance between the first implantable microelectronic device and each of the plurality of second implantable microelectronic devices.

6. The system of claim 1, wherein the first implantable microelectronic device and the plurality of the second implantable microelectronic devices are less than 6 mm in lateral dimension and less than 60 mm in axial dimension.

7. A system for determining relative positions of body parts, the system comprising:
    a first subsystem, comprising:
        a first implantable microelectronic device adapted to emit magnetic signals having a first frequency;
        a plurality of second implantable microelectronic devices adapted to receive the magnetic signals having the first frequency;
    a second subsystem, comprising:
        a third implantable microelectronic device adapted to emit magnetic signals having a second frequency;
        a plurality of fourth implantable microelectronic devices adapted to receive the magnetic signals having the second frequency;
    a controller in communication with the first implantable microelectronic device, the plurality of second implantable microelectronic devices, the third implantable microelectronic device and the plurality of fourth implantable microelectronic devices.

8. The system of claim 7, wherein the plurality of second implantable microelectronic devices and the plurality of fourth implantable microelectronic devices each comprise a resonator having a predetermined bandwidth.

9. The system of claim 8, wherein the first frequency and the second frequency fall within the resonator bandwidth.

10. The system of claim 9, wherein each of the plurality of second implantable microelectronic devices and the plurality of fourth implantable microelectronic devices comprise a signal processor means, whereby each selectively processes the magnetic signals having the first frequency and the second frequency to determine the strength of the magnetic signals received.

11. The system of claim 10, wherein the first implantable microelectronic device, the plurality of second implantable microelectronic devices, the third implantable microelectronic device and the plurality of fourth implantable microelectronic devices are less than 6 mm in lateral dimension and less than 60 mm in axial dimension.

12. A system for determining relative positions of body parts, the system comprising:
    a first microelectronic device adapted to emit magnetic signals having a first frequency;
    a plurality of second microelectronic devices adapted to receive the magnetic signals having the first frequency; said first and second microelectronic devices suitable for subcutaneous injection by an insertion tool;
    a controller in communication with the first microelectronic device and the plurality of the second microelectronic devices.

* * * * *